(12) United States Patent
Ghoneum et al.

(10) Patent No.: US 8,486,465 B1
(45) Date of Patent: Jul. 16, 2013

(54) THERAPEUTIC NERIUM OLEANDER EXTRACT COMPOSITIONS AND METHODS OF USING

(75) Inventors: Mamdooh Ghoneum, Los Angeles, CA (US); Huseyin Ziya Ozel, Gayrettepe (TR)

(73) Assignee: Douglas Crawford, Colona, IL (US)

( * ) Notice: Subject to any disclaimer, the term of this patent is extended or adjusted under 35 U.S.C. 154(b) by 0 days.

(21) Appl. No.: 13/247,894

(22) Filed: Sep. 28, 2011

Related U.S. Application Data

(63) Continuation of application No. 12/218,134, filed on Jul. 9, 2008.

(60) Provisional application No. 60/959,028, filed on Jul. 9, 2007.

(51) Int. Cl.
*A61K 36/13* (2006.01)
*A61K 39/40* (2006.01)

(52) U.S. Cl.
USPC .......................................... 424/770; 424/1.69

(58) Field of Classification Search
None
See application file for complete search history.

(56) References Cited

U.S. PATENT DOCUMENTS

| 5,135,745 | A | * | 8/1992 | Ozel ............................. 424/725 |
| 6,565,897 | B2 | * | 5/2003 | Selvaraj et al. ............... 424/725 |
| 2002/0022022 | A1 | * | 2/2002 | Shi et al. ...................... 424/94.4 |
| 2004/0082521 | A1 | | 4/2004 | Singh |
| 2005/0026849 | A1 | | 2/2005 | Singh et al. |
| 2006/0188536 | A1 | * | 8/2006 | Addington .................... 424/405 |
| 2006/0188585 | A1 | | 8/2006 | Panosyan et al. |
| 2006/0205679 | A1 | | 9/2006 | Streeper et al. |
| 2007/0026092 | A1 | | 2/2007 | Addington |
| 2007/0154573 | A1 | | 7/2007 | Rashan et al. |

OTHER PUBLICATIONS

The guardian at www.guardian.co.uk/science/2012/may/09/cancers-treatable-infections.*

* cited by examiner

*Primary Examiner* — Chris R Tate
*Assistant Examiner* — Deborah Davis
(74) *Attorney, Agent, or Firm* — Koppel, Patrick, Heybl & Philpott

(57) ABSTRACT

The compositions and methods described herein relate generally to therapeutic compositions containing *Nerium* species extracts, as well as to methods for treating diseases or disorders by administering the compositions, including compositions having a combination of *Nerium* species extract and glutathione. It further includes pharmaceutical compositions containing a combination of glutathione and a *Nerium* species extract. The compositions and methods disclosed may be useful for treating a variety of diseases or disorders including one or more cell-proliferative diseases or disorders, infections, and dementias.

18 Claims, 3 Drawing Sheets

THERAPEUTIC NERIUM OLEANDER EXTRACT COMPOSITIONS AND METHODS OF USING

CROSS REFERENCE TO RELATED APPLICATION

This application is a continuation of U.S. patent application Ser. No. 12/218,134 filed Jul. 9, 2008 and claims the benefit of U.S. Provisional Application No. 60/959,028 filed on Jul. 9, 2007.

BACKGROUND

1. Field of the Invention

The compositions and methods provided herein relate generally to therapeutic compositions that include extracts derived from Nerium species and methods of treatment using the compositions.

2. Description of the Related Art

Glutathione (GSH) is a tripeptide synthesized by the liver from three amino acids: glutamic acid, cysteine and glycine. The tripeptide contains an unusual peptide linkage between the amine group of cysteine and the carboxyl group of the glutamate side chain. Because it is synthesized in the body, glutathione is not considered an essential nutrient. However, in cases of increased exposure to toxic substances or reactive oxygen species, as is often the case in disease states, its rate of synthesis may be lower than the rate of turnover, in which case glutathione becomes a "conditionally essential nutrient". Diet can contribute significant amounts of glutathione, which can be reasonably well absorbed in the intact state and is resistant to digestion because of the atypical nature of the amino acid bonds in the peptide (as compared to those typically found in dietary protein).

Glutathione, an antioxidant, protects cells from toxic substances such as free radicals (e.g. reactive oxygen species) and has been shown to prevent cancer development in animal models. Low dietary glutathione has been associated with increased incidence of oral and pharyngeal cancer. The administration of N-acetylcysteine has been reported to increase glutathione levels and to help reduce chemically induced lung tumors in animals. In response to increased interest in glutathione as a cancer preventive/resistive substance, the National Cancer Institute has been compiling data on the glutathione content of foods. The function of glutathione as a nutrient having cancer preventive properties, and its relationship to diet and detoxification activity, continue to be a rich research area which may provide new opportunities for preventing or treating cancer and other diseases.

The term "oleander" refers to two plant species, Nerium oleander (common oleander) and Thevetia peruviana (yellow oleander) which grow in temperate climates throughout the world. Both species contain chemicals called cardiac glycosides which have effects similar to the heart drug digoxin and can be toxic when taken by mouth, with many documented reports of deaths. It is estimated that as many as 100 chemical substances are present in various parts of the oleander plant. Laboratory studies of oleander suggest possible anti-cancer effects, although reliable research in humans has not yet been performed. There are also reports that long-term use of oleander may have positive effects in patients with leiomyosarcoma, Ewings's sarcoma, prostate or breast cancer. Oleander has also been used for other medicinal purposes including itchiness relief, hair loss prevention, syphilis treatment, as a gargle to strengthen teeth and gums, and as a nose drop for children.

Nerium oleander (N. oleander) is a common ornamental evergreen shrub which is used as a freeway median divider in warmer states such as California. This plant is extremely toxic and a single leaf may kill an adult. The toxicity of N. oleander is derived primarily from the presence of the cardiac glycoside oleandrin. Nerium oleander leaf extracts have recently completed Phase 1 clinical evaluation as a potential treatment for cancer.

Non-toxic, water-soluble extracts of N. oleander have been used in the treatment of various cancers and dementias, and also to boost the immune system in healthy subjects as described in U.S. Pat. No. 5,135,745 and U.S. Pat. No. 6,565,897 which are incorporated herein by reference in their entirety. The characterization of the biological activity of the extracts suggested that their activity potentiates an immune response by modulating the effects of cells in the immune system. The water-soluble extracts contained, among other ingredients, one or more immunologically active polysaccharides which may be useful in treating cell-proliferative disease in mammals. The results of such treatments have suggested that Nerium species extracts may be useful as non-toxic therapeutic agents to treat a variety of diseases or disorders including malignant and non-malignant cell proliferative diseases and disorders, infectious diseases, immune deficient diseases, dementias and pain. However, although the therapeutic use of such extracts has ameliorated or suppressed diseases in many patients, it has proven difficult to get a consistent response to the extracts in most or all patients and some patients did not respond at all.

Although methods for providing extracts of Nerium species have been disclosed which do not require a polar inorganic solvent such as water in the extraction process, those approaches suffer from the disadvantage that the alternative technologies and processes used can reduce or alter the amount, number, type, or activity of therapeutically beneficial components in the extract, including immunologically active polysaccharides. The therapeutic potential of such extracts can therefore be highly dependent upon the particular compounds retained therein as a result of the nature of the extraction process.

What is needed therefore are non-toxic Nerium species extracts and which, either alone or in conjunction with other agents or compounds, can provide clinically useful and consistent therapeutic benefits, preferably for a wide variety of diseases at relatively low concentrations.

SUMMARY

Briefly, and in general terms, the embodiments described herein are directed to extracts of Nerium species and therapeutic uses thereof.

In particular, the embodiments described herein include one or more compositions comprising combinations of Nerium species extracts and GSH having therapeutically useful activities, as well as methods for treating various diseases by administering the one or more compositions to a subject.

These and other aspects and advantages of the embodiments will become apparent from the following detailed description and the accompanying drawings, which are illustrative and not limiting.

DETAILED DESCRIPTION

Figure 1A:
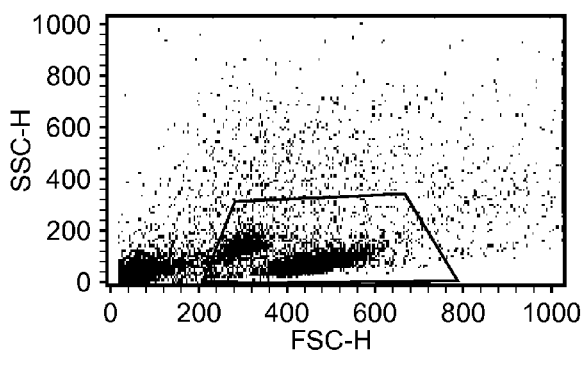
FIG. 1A is a flow cytometry dot-plot of a control showing MCF-7 cancer cells cultured in the absence of Nerium oleander extracts (NOE) and GSH.

The following description presents preferred embodiments of the invention representing the best mode contemplated for practicing the compositions and methods described herein. This description is not to be taken in a limiting sense, but is made merely for the purpose of describing the general principles of the embodiments. For the sole purpose of convenience and ease of understanding, reference is made in the illustrative embodiments to *Nerium oleander* extract (NOE).

The compositions and methods provided herein are directed to new *Nerium* species extract compositions and uses thereof which have the potential to provide, at relatively low concentrations, clinically useful and consistent therapeutic benefits to subjects having solid tumors and possibly to those having other diseases.

Other features and advantages of the invention will be apparent from the following detailed description when taken together with the drawings, and from the claims.

Before addressing details of embodiments described below, some terms are defined or clarified. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the embodiments disclosed herein. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present embodiments, examples of suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following definitions refer to the particular embodiments described herein and are not to be taken as limiting; the embodiments include equivalents for other undescribed embodiments.

As used herein, the term "cell proliferative" when referring to diseases or disorders is intended to mean diseases associated with abnormal cell proliferation, including without limitation those resulting in malignant as well as non-malignant cell populations which often appear morphologically to differ from the surrounding tissue including without limitation cancer, psoriasis, and diseases associated with unregulated angiogenesis including growth and metastasis of solid tumors, ocular diseases, retinopathies, or arthritis.

As used herein, the term "infectious disease" is intended to mean disorders arising from infectious biological agents including without limitation viral, bacterial, protozoan and fungal infections.

As used herein, the term "subject" is intended to mean one that is acted on during the course of treatment, including without limitation a human or non-human animal awaiting or under medical care or treatment.

As used herein, the term "treating" or "treatment" with respect to the extract is meant to include both in vitro and in vivo diagnosis as well as the in vivo amelioration or suppression of diseases or disorders or symptoms thereof.

Attention is now directed to more specific details of embodiments that illustrate but not limit the invention. The present embodiments relate to compositions that include *Nerium* species extracts and therapeutic uses thereof.

One embodiment of the present invention utilizes a composition which includes a *Nerium oleander* extract (NOE) and glutathione (GSH) to ameliorate cell proliferative diseases as described below.

*N. oleander* extracts (NOEs) were used in the current study to investigate their potential for increasing tumor cell apoptosis post treatment with GSH in vitro. The flow cytometry and microscopic analysis of cancer cell apoptosis in these studies showed that treatment with NOE alone may induce programmed cell death, in a dose dependent manner, and that the addition of GSH to the treatment protocol can enhance the effects of NOE, also in a dose dependent manner. However, surprisingly, the effect of using NOE in combination with GSH can be synergistic rather than additive, providing a significantly elevated response in comparison to those achieved with either GSH or NOE alone. These in vitro data show that treatment of a human subject with a combination of NOE and GSH may, where synergism occurs, similarly provide a significantly enhanced and therefore more consistent and effective response to a particular disease relative to that achieved by treatment with NOE or GSH alone.

These results suggest that NOE may be of potential value in the prevention or treatment of disorders arising from deleterious anti-proliferative or anti-angiogenic activities, including without limitation the treatment of solid tumors. Furthermore, combinations of such compositions containing different types or amounts of *Nerium* species extract and GSH could potentially provide further benefit via additional unanticipated synergism. The concentration or amount (e.g. weight) of NOE or GSH which is safe and effective for use, either therapeutically or diagnostically, may vary depending upon the application desired, and therefore the most effective concentration for any one particular use may be significantly higher (including without limitation 300 µg/ml NOE or 50 mM GSH) or lower (including without limitation 0.01 µg/ml NOE or 0.1 mM GSH) than those disclosed for the embodiments described herein.

METHODS

Preparation of *Nerium Oleander* Extract.

The production of the *Nerium oleander* extract is generally similar to the hot water extraction technique disclosed in U.S. Pat. No. 5,135,745, the contents of which are hereby incorporated by reference. Hot water extraction provides *Nerium* species extracts which contain a variety of components including without limitation immunologically active polysaccharides. Preferred species of *Nerium* for preparation of extracts are *N. indicuim* and *N. oleander*.

The term "plant matter" denotes any part of the plant, although the less fibrous parts of the plant (branches, leaves flowers) are generally more useful than fibrous parts such as, for example, roots or lower, woody parts of stems. The extracts of the embodiments are preferably prepared from the branches, leaves and flowers of the *Nerium oleander* plant which can be sliced into pieces preferably ranging in size from about 2 cm to about 2.5 cm in length. Within about 1 week of collecting and slicing the plant material, the sliced plant material is suspended in a polar inorganic solvent, such as water, and heated to about 100° C. Heating at about 100° C. was continued for about 2.5 hours, during which time loss of liquid due to evaporation is compensated for by the addition of water to the vessel. At the end of the initial heat treatment, the density of the aqueous phase is determined. If the density is less than about 1010 kg/m$^3$ (1.01 gm/cc), the extract is again heated until the desired density is obtained. After the proper density is obtained, the mixture is allowed to cool to room temperature, filtered to remove large particulate matter, filtered again to eliminate small particulate matter, aliquoted into appropriate containers and sealed. After this second filtration, the sealed containers are again heated to about 100° C. for about 1 hour. Following this second heat treatment, the bottles are stored at room temperature for about 10 hours. In this form, the extract has a shelf life of about one year when stored between about 2° C. and 4° C.

Cell Culture. Human breast cancer MCF-7 cells were cultured with varying concentrations of only GSH (0, 2.5, 5 and 10 mM), only NOE (0, 50 and 100 µg/ml), or with GSH and NOE in combination for 24 hours. Control samples contained neither GSH nor NOE. Levels of apoptosis (cell death) were then examined using the Propidium Iodide technique as measured by flow cytometry using a FACscan (BD Biosciences, San Jose, Calif.). Forward (FSC) and Side scatter (SSC) were used to gate the cells. The MCF-7 cells were obtained from American Type Culture Collections (ATCC) (Rockville, Md.) and the GSH from Sigma Chemical Company (St Louis, Mo.).

Combination Therapy.

MCF-7 cells were incubated with varying concentrations of GSH for 4 hours before the addition of NOE. Cells were examined for apoptosis at 24 hours post treatment with GSH.

Cell Viability Assay.

MCF-7 cells incubated with GSH alone, NOE alone, or with GSH and NOE in combination were evaluated for cell survival using an MTT ((3-(4,5-Dimethylthiazol-2-yl)-2,5-diphenyltetrazolium bromide) assay.

Compositions and Kits.

The *Nerium* species extract can be administered to a subject by any suitable route that ensures bioavailability in the circulation of the subject. This can often best be achieved by parenteral routes of administration including intravenous, intramuscular, intradermal, subcutaneous and intraperitoneal injections. However, other routes of administration can be used. For example, absorption through the gastrointestinal tract can be accomplished by oral routes of administration, including but not limited to, ingestion, buccal and sublingual routes.

In one embodiment, the compositions can be administered transcutaneously (e.g. transdermally or topically) or by inhalation. It will be appreciated that the preferred route can vary with the condition, age and compliance of the subject.

In another embodiment, kits are provided comprising a composition comprising at least one *Nerium* species extract, glutathione and an additional composition for the treatment or amelioration of the disease, disorder or infection. For example, in a kit for the treatment or amelioration of infection, the composition comprising *Nerium* species extract and glutathione can further include medicaments for the treatment of infection such as an antibiotic, antipyretic, cough suppressant and the like.

According to another aspect, kits are provided containing, for example, a composition comprising a *Nerium* species extract and glutathione and a medicament for the treatment or amelioration of a malignancy.

EXAMPLES

Example 1

Preparation of *Nerium Oleander* Extract.

The branches, leaves and flowers of *Nerium oleander* were collected and sliced into pieces from about 2 to about 2.5 cm in length. Within about one week following collection and slicing of the plant material, an extract was prepared from the plant material by adding approximately 2 kg of sliced plant material to about 10 kg of distilled water in an enamel container. This mixture of material was heated until it started boiling, after which time the plant material was boiled for about 2.5 hours. During boiling, distilled water was added to the container to compensate for evaporation, in order to maintain a constant water level in the container. At the end of about 2.5 hours of boiling, the density of the aqueous phase extract was about 1010 kg/m$^3$, as measured using a buoyancy densitometer. If the density was less than about 1010, the extract was boiled for about another half hour until the desired density was attained through further evaporation. After boiling, the mixture was allowed to stand at room temperature for a period of about 6 to about 8 hours. Next, the mixture was processed through a coarse filter in order to remove any large particulate matter such as leaves and branches. The filtrate was then subjected to a second filtration through a medical filter and decanted into 700 ml bottles having tight lids. Within about 4 hours after this last filtration step, the bottles were heated to about 100° C. for about 1 hour. Following this second heat treatment, the bottles were stored at room temperature for about 10 hours. In this form, the extract can have a shelf life of up to about one year when stored at about 2° C. to about 4° C. Filters known and used in the art are suitable for the methods of making the extract and compositions provided herein.

Example 2

Human breast cancer MCF-7 cells were cultured with GSH alone (5 mM), NOE alone (50 μg/ml), or with 5 mM GSH and 50 μg/ml NOE in combination for 24 hours. The control sample contained neither GSH nor NOE.

Figure 1B:
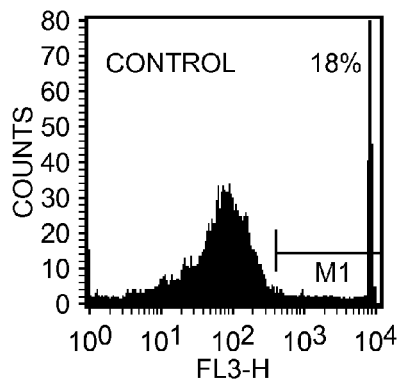
FIG. 1B is a frequency histogram of the data shown in FIG. 1A showing the total population (18%) of apoptotic MCF-7 cancer cells (control)
Figure 1C:
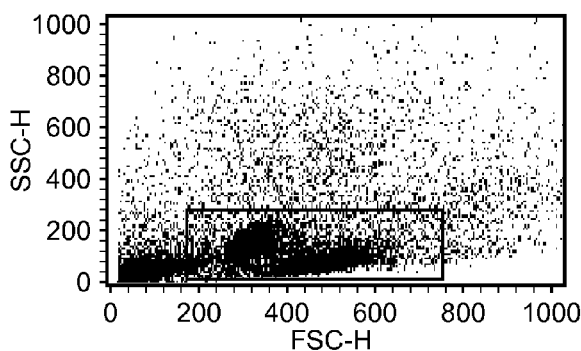
FIG. 1C is a flow cytometry dot-plot showing MCF-7 cancer cells cultured in the presence of 5 mM GSH.
Figure 1D:
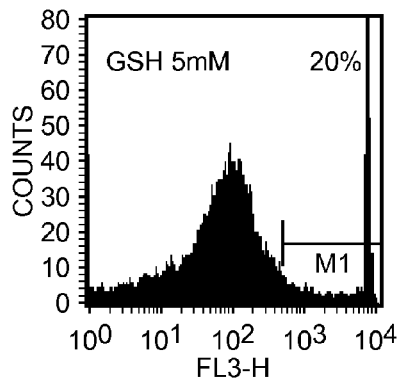
FIG. 1D is a frequency histogram of the data shown in FIG. 1C showing the total population (20%) of apoptotic MCF-7 cancer cells.
Figure 1E:
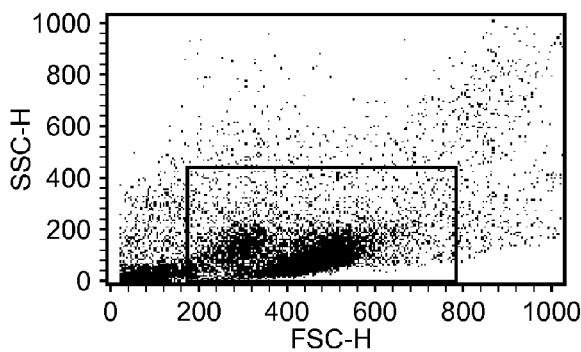
FIG. 1E is a flow cytometry dot-plot showing MCF-7 cancer cells cultured in the presence of 50 µg/ml NOE.
Figure 1F:
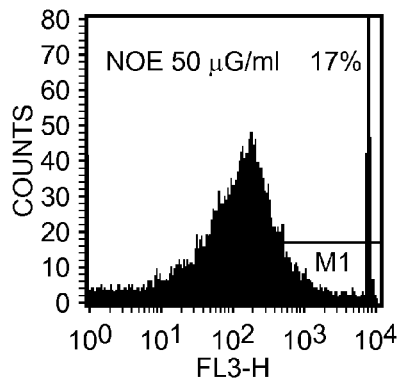
FIG. 1F is a frequency histogram of the data shown in FIG. 1E showing the total population (17%) of apoptotic MCF-7 cancer cells.
Figure 1G:
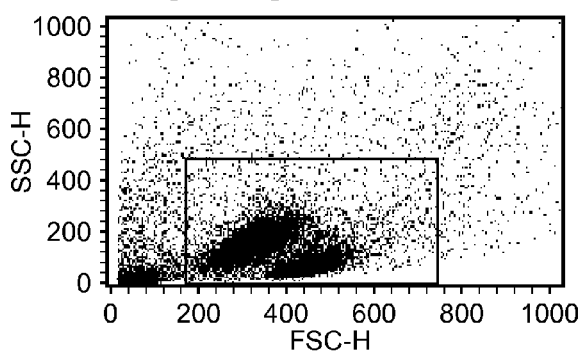
FIG. 1G is a flow cytometry dot-plot showing MCF-7 cancer cells cultured in the presence of 5 mM GSH and 50 µg/ml NOE.
Figure 1H:
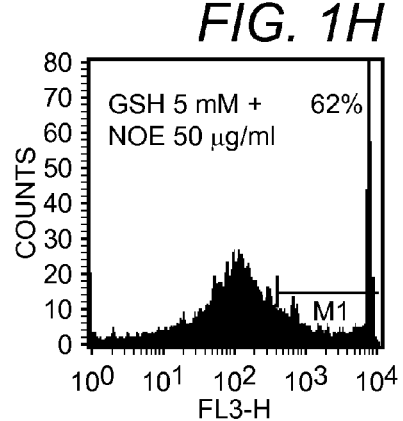
FIG. 1H is a frequency histogram of the data shown in FIG. 1G showing the total population (62%) of apoptotic MCF-7 cancer cells.

FIGS. 1A-1G show forward scatter (FSC-H), side scatter (SSC-H) and F13 channel fluorescence (F13-H) flow cytometry data for MCF-7 cells grown in the presence or absence of 5 mM GSH and/or 50 μg/ml NOE. FIGS. 1A, 1C, 1E, and 1G are dot plots which show the populations of cells grown under the particular culture conditions described below, while FIGS. 1B, 1D, 1F, and 1H respectively are the corresponding frequency histograms showing the total population of apoptotic MCF-7 cancer cells for each culture. FIGS. 1A-1B shows control data for cells grown in the absence of GSH and NOE, where about 18% cancer cell apoptosis was detected. FIGS. 1C-1D are the data for cells grown in the presence of 5 mM GSH, where about 20% cancer cell apoptosis was detected. FIGS. 1E-1F are the data for cells grown in the presence of 50 μg/ml NOE, where about 17% cancer cell apoptosis was detected. Therefore, the level of apoptosis for 5 mM GSH as shown in FIGS. 1C-1D and 50 μg/ml NOE as shown in FIGS. 1E-1F were comparable in this study. FIGS. 1G-1H are the data for cells grown in the presence of both 5 mM GSH and 50 μg/ml NOE, where about 62% cancer cell apoptosis was detected. In comparison to the data shown FIGS. 1A-1B, FIGS. 1C-1D and FIGS. 1E-1F, it was readily apparent that GSH and NOE were acting synergistically in that the total effect of the GSH+NOE combination was significantly greater than the sum of the individual effects for GSH or NOE alone.

Therefore, as illustrated below in Table 1, the combination of NOE and GSH unexpectedly provided a highly synergistic effect with respect to apoptosis. These results suggest that NOE may be of potential value in the treatment of solid and/or immune resistant cancers.

TABLE 1

Cell Apoptosis in 0-50 μg/ml NOE and 0-5 mM GSH

| NOE (μg/ml) | GSH (mM) | % cell survival | % cell death | % cell survival relative to Control | % cell death relative to control |
|---|---|---|---|---|---|
| 0 | 0 | 82 | 18 | 100 | 0 |
| 0 | 5 | 80 | 20 | 98 | 11 |
| 50 | 0 | 83 | 17 | 101 | −6 |
| 50 | 5 | 38 | 62 | 46 | 244 |

Example 3

Figure 2A:
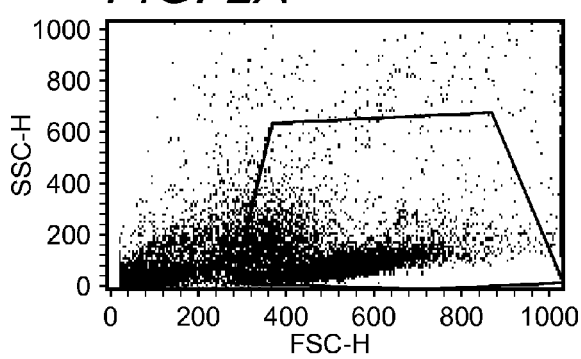
FIG. 2A is a second flow cytometry dot-plot showing MCF-7 cancer cells cultured in the absence of NOE and GSH (control)
Figure 2B:
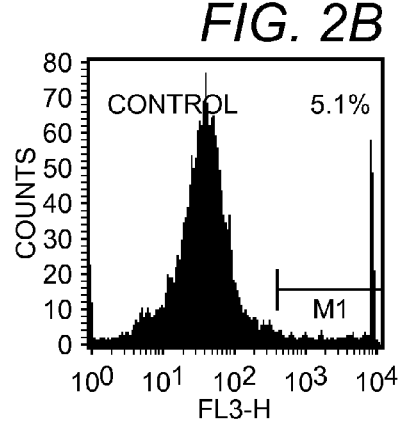
FIG. 2B is a frequency histogram of the data shown in FIG. 2A showing the total population (5.1%) of apoptotic MCF-7 cancer cells (control)
Figure 2C:
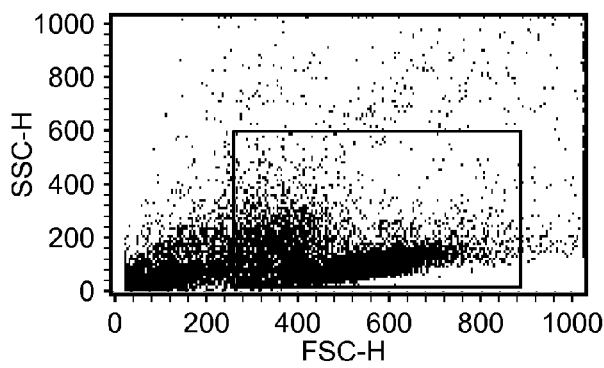
FIG. 2C is a second embodiment flow cytometry dot-plot showing MCF-7 cancer cells cultured in the presence of 10 mM GSH.
Figure 2D:
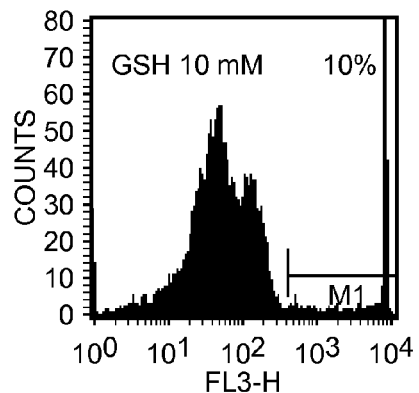
FIG. 2D is a frequency histogram of the data shown in FIG. 4C showing the total population (10%) of apoptotic MCF-7 cancer cells.
Figure 2E:
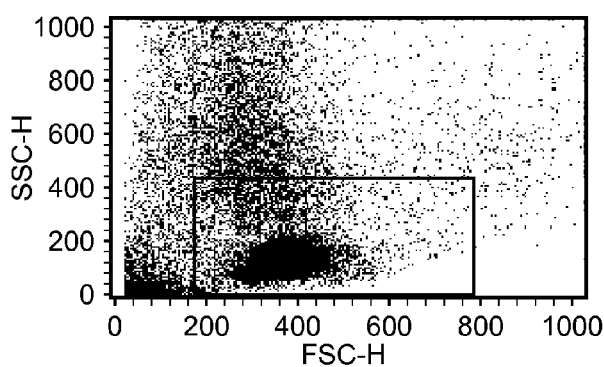
FIG. 2E is a second embodiment flow cytometry dot-plot showing MCF-7 cancer cells cultured in the presence of 50 µg/ml NOE.
Figure 2F:
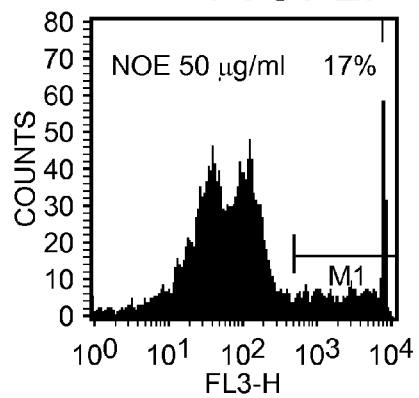
FIG. 2F is a frequency histogram of the data shown in FIG. 4E showing the total population (17%) of apoptotic MCF-7 cancer cells.
Figure 2G:
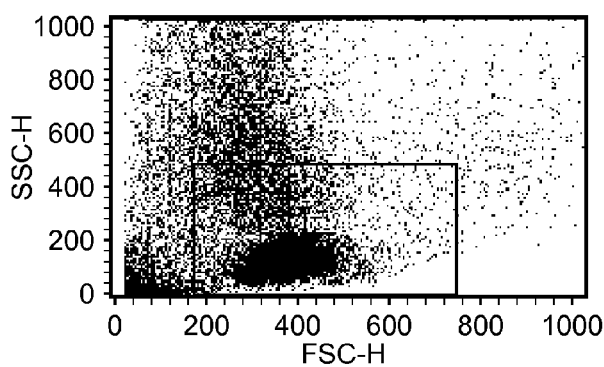
FIG. 2G is a second embodiment flow cytometry dot-plot showing MCF-7 cancer cells cultured in the presence of 10 mM GSH and 50 µg/ml NOE.
Figure 2H:
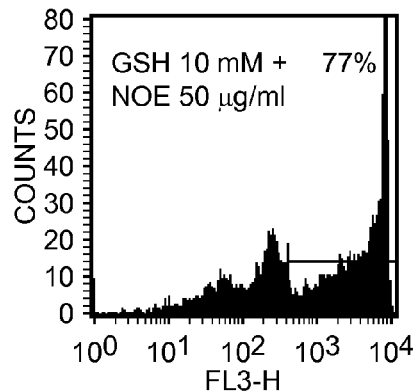
FIG. 2H is a frequency histogram of the data shown in FIG. 4G showing the total population (77%) of apoptotic MCF-7 cancer cells.

A series of experiments identical to those described in Experiment 1 one were carried out using a slightly higher concentration of GSH (i.e. 10 mM rather than 5 mM). FIGS. 2A-2H show forward scatter (FSC-H), side scatter (SSC-H) and F13 channel fluorescence (F13-H) flow cytometry data for MCF-7 cells grown in the presence or absence of 10 mM GSH and/or 50 μg/ml NOE. FIGS. 2A, 2C, 2E, and 2G are dot plots which show the populations of cells grown under the particular culture conditions described below, while FIGS. 2B, 4D. 4F, and 2B, 2D, 2F and 2H respectively are the corresponding frequency histograms showing the total population of apoptotic MCF-7 cancer cells for each culture. FIGS. 2A-2B shows control data for cells grown in the absence of GSH and NOE, where about 5.1% cancer cell apoptosis was detected. FIGS. 2C-2D are the data for cells grown in the presence of 10 mM GSH, where about 10% cancer cell apoptosis was detected. FIGS. 2E-2F are the data for cells grown in the presence of 50 μg/ml NOE, where about 17% cancer cell apoptosis was detected. The data in FIGS. 2E-2F showed that treatment with NOE alone can induce programmed cell death and, in comparison to the data shown in FIGS. 2C-2D, to a relatively greater extent than treatment with GSH alone. FIGS. 2G-2H shows data for cells grown in the presence of both 10 mM GSH and 50 μg/ml NOE, where about 77% cancer cell apoptosis was detected. By comparing the data shown in FIGS. 1G-1H to those in FIGS. 2G-2H, respectively, it is clear that the addition of GSH (5 mM or 10 mM, respectively) to the NOE treatment protocol enhances the effects of NOE in a dose dependent manner, in that 5 mM GSH was less effective than 10 mM GSH with respect to cell death (62% to 77% respectively).

Additionally, when comparing the data in FIGS. 2A-2H to the corresponding data in FIGS. 1A-1H, it appears that the level of apoptosis for the control in that experiment may have been erroneously high in that it was more similar to that of GSH alone (10 mM), and NOE alone (50 μg/ml) as shown above in FIGS. 1A-1B, 1C-1D, and FIGS. 1E-1F respectively. However, as illustrated in Table 1 above and in Table 2 below, the combination of NOE and GSH in both examples clearly and unexpectedly provided a highly synergistic effect with respect to apoptosis which can provide a significant and therapeutically practical advantage with respect to the treatment of cell proliferative diseases and disorders.

TABLE 2

Cell Apoptosis in 0-50 μg/ml NOE and 0-10 mM GSH

| NOE (μg/ml) | GSH (mM) | % cell survival | % cell death | % cell survival relative to Control | % cell death relative to control |
|---|---|---|---|---|---|
| 0 | 0 | 94.9 | 5.1 | 100 | 0 |
| 0 | 10 | 90 | 10 | 95 | 96 |
| 50 | 0 | 83 | 17 | 88 | 233 |
| 50 | 10 | 23 | 77 | 24 | 1410 |

The embodiments and examples set forth herein were presented to explain the general nature of the invention and its practical application, and thereby to enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, while specific reference was made in this specification to embodiments having *Nerium oleander* extract (NOE), the invention contemplated is not so limited. Those of skill in the art will appreciate that various species of the *Nerium* genus may be contemplated or used without departing from the spirit and scope of the invention as defined in the appended claims.

We claim:

1. A composition for treating a cell-proliferative disease or disorder comprising a synergistic combination of glutathione and a *Nerium* extract in amounts effective to induce and enhance apoptosis, wherein the concentration of said glutathione is 5 mM to 10 mM and the concentration of said *Nerium* extract is 50 ug/ml to 100 ug/ml within the composition.

2. The composition of claim 1, wherein the *Nerium* species is *Nerium oleander*.

3. The composition of claim 1, wherein the combination is immunologically active.

4. The composition of claim 1, wherein the *Nerium* extract is a water soluble extract.

5. The composition of claim 1, wherein the *Nerium* extract is a polysaccharide-enriched extract.

6. The composition of claim 1, wherein the composition is a pharmaceutical composition.

7. The composition of claim 1, wherein the *Nerium* extract is obtained by a method comprising:
dispersing plant matter derived from a *Nerium* species in a polar inorganic solvent;
heating the dispersed plant matter in the solvent;
separating the heated solvent from the plant matter; and
heating the separated solvent.

8. The composition of claim 7, wherein the polar inorganic solvent is water.

9. The composition of claim 7, wherein the heating of the plant matter in the solvent is carried out for a time sufficient to obtain a solvent density of about 1010 kg/m$^3$.

10. The composition of claim 7, wherein the *Nerium* species is *Nerium oleander*.

11. The composition of claim 7, wherein the method of obtaining the *Nerium* species extract further comprises:
filtering the heated solvent; and
heating the filtered solvent.

12. A method for treating at least one cell-proliferative disease or disorder comprising administering to a subject in need thereof a composition comprising a synergistic combination of glutathione and a *Nerium* extract in amounts effective to induce and enhance apoptosis, wherein the concentration of said glutathione is 5 mM to 10 mM and the concentration of said *Nerium* extract is 50 ug/ml to 100 ug/ml within the administered composition.

13. The method of claim 12, wherein the subject is a mammal.

14. The method of claim 12, wherein the administration is parenteral, enternal or oral.

15. The method of claim 14, wherein the *Nerium* species is *Nerium oleander*.

16. The method of claim 12, wherein the at least one cell-proliferative disease or disorder is caused by a viral, bacterial, protozoan or fungal infection, or a combination thereof.

17. The method of claim 12, wherein the at least one cell-proliferative disease or disorder is a malignancy, a non-malignancy, or a combination thereof.

18. The method of claim 17, wherein the at least one cell-proliferative disease or disorder is a malignancy, and wherein the malignancy is breast cancer or lymphoma.

* * * * *